United States Patent
Saslawski et al.

(10) Patent No.: US 6,372,255 B1
(45) Date of Patent: Apr. 16, 2002

(54) TABLET FOR INSTANT AND PROLONGED RELEASE OF ONE OR MORE ACTIVE SUBSTANCES

(75) Inventors: Olivier Saslawski, Haquenau; Laurence Orlando, Decines, both of (FR)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/581,992
(22) PCT Filed: Dec. 11, 1998
(86) PCT No.: PCT/EP98/08100
§ 371 Date: Jun. 21, 2000
§ 102(e) Date: Jun. 21, 2000
(87) PCT Pub. No.: WO99/33448
PCT Pub. Date: Jul. 8, 1999

(30) Foreign Application Priority Data
Dec. 23, 1997 (FR) .............................. 97-16402

(51) Int. Cl.[7] .............................. A61K 9/24; A61K 9/26
(52) U.S. Cl. .................. 424/473; 424/472; 424/470; 424/469; 424/468; 424/474; 514/770; 514/772.3; 514/778; 514/779; 514/781; 514/782; 514/826

(58) Field of Search .................................. 424/472, 473, 424/474, 475, 479, 480, 484, 471, 469, 470, 468

(56) References Cited

U.S. PATENT DOCUMENTS

| 4,359,483 A | 11/1982 | Kaetsu et al. .................. 427/2 |
| 4,752,479 A | * 6/1988 | Briggs et al. .............. 424/472 |
| 6,033,685 A | * 3/2000 | Qui et al. .................... 424/464 |

FOREIGN PATENT DOCUMENTS

| EP | 0 169 821 | 1/1986 |
| FR | 2 645 152 | 10/1990 |

* cited by examiner

Primary Examiner—James M. Spear
(74) Attorney, Agent, or Firm—Millen, White, Zelano & Branigan, P.C.

(57) ABSTRACT

A multi-layer tablet for the instant and prolonged release of active substances comprises at least two layers where the first outer layer comprises a mixture of excipients and an active substance, allowing for the immediate release of the active substance within the first layer, and a second layer, arranged in contact with the first layer. The second layer comprises a nonbiodegradable inert porous polymeric matrix in which an active substance is dispersed, allowing for the prolonged release of the active substance within the second layer.

18 Claims, 4 Drawing Sheets

TABLET FOR INSTANT AND PROLONGED RELEASE OF ONE OR MORE ACTIVE SUBSTANCES

This application is a 371 of PCT/EP98/08100 filed Dec. 11, 1998.

The invention relates to solid galenic forms of the controlled release tablet type for the instant and then prolonged release of one or more active substances.

The importance of such galenic forms is undeniable. The immediate release of an active substance will ensure its practically instant bioavailability, which is particularly desirable in the case of patients suffering from acute conditions.

However, in the case of active substances having a short half-life, the therapeutic activity is only temporary. Now, a continuous and regular supply of active ingredient is often necessary for an effective therapy. To this end, numerous immediate- and prolonged-release systems have been developed.

Reference may be made, for example, to the following patents and applications of the state of the art: WO 96/03111, U.S. Pat. No. 4,990,335, EP 352 190, BE 905 282, EP 106 443, EP 36 350, EP 615 444 and EP 220 670.

However, in the prior art systems, the kinetics of release of the active ingredient depend on many factors, such as the enzymatic activity and the pH conditions which vary substantially from one individual to another and for the same individual, depending on whether they are on an empty stomach or not.

Furthermore, the pH conditions vary all along the gastrointestinal tract. Thus, it is difficult to predict in vivo, with precision, the profile for the release of a given substance after administration of the prior art instant- and prolonged-release systems.

The present invention aims to solve this problem by providing tablets which preserve their characteristics for the release of active substances regardless of the conditions of administration in vivo.

Figure 1:
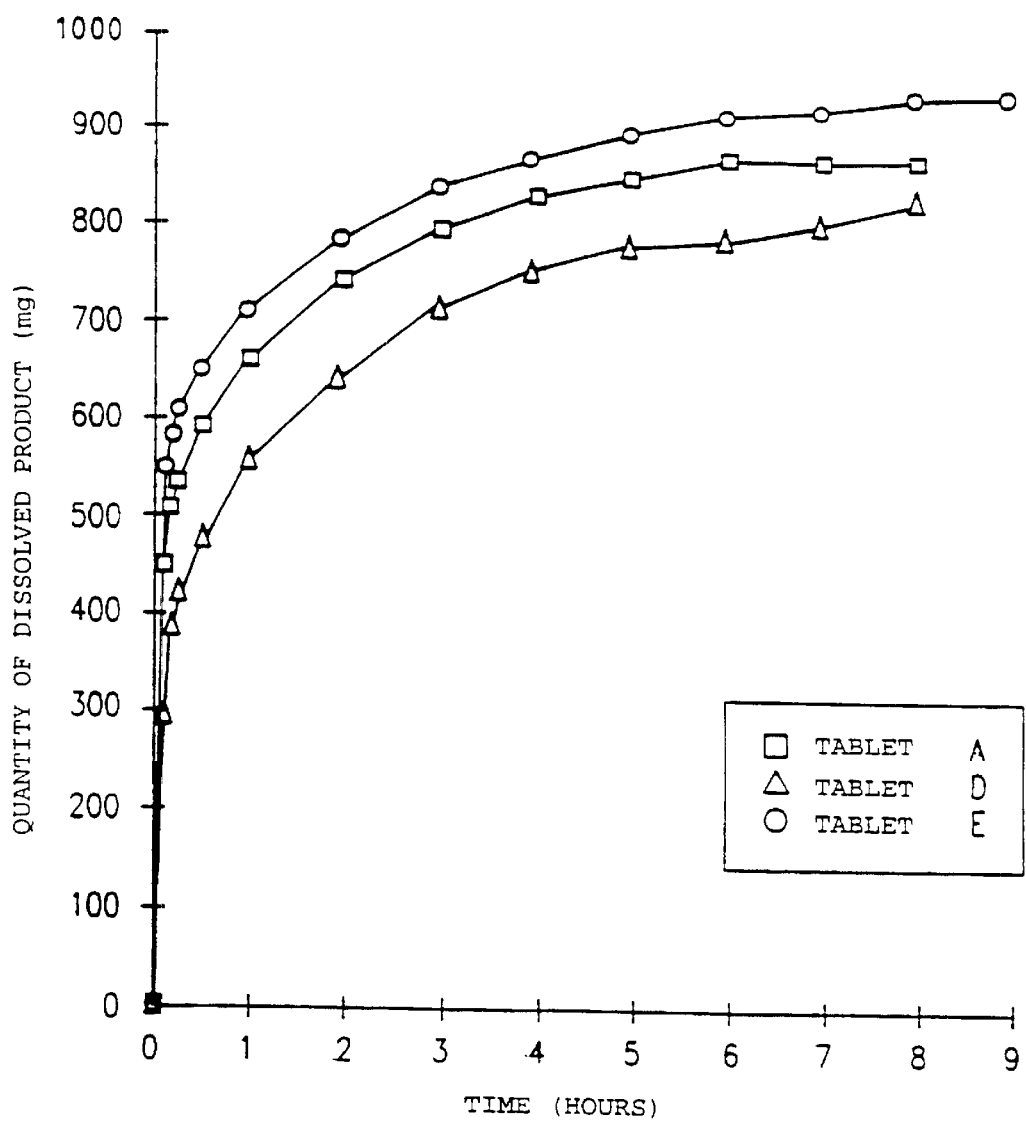
FIGS. 1–6 show dissolution profiles for the tablets in Tables 1 and 2 of the invention.

The tablets of the invention provide an excellent reproducibility of the results, while allowing an increased control of the rates of release during the phase of prolonged release of the active ingredient. By using the tablets of the invention, it becomes possible to optimize the supply of the active ingredients in the body while taking into account both the subject's tolerance to the active ingredient and the pharmacokinetic and metabolic profiles of the active ingredient.

Tablets of the invention are, moreover, advantageous from the point of view of the formulation of the active ingredients since a judicious choice of the excipients leads to tablets with high concentrations of active ingredients.

Thus, it is possible to produce tablets with very high doses, having an acceptable size for oral administration.

More precisely, the invention relates to multilayer tablets for the instant and then prolonged release of active substances comprising at least two superposed layers, characterized in that:

a first outer layer is composed of a mixture of excipients and of a first active substance, the said first layer allowing immediate release of the said first active substance;

a second layer, arranged in contact with the said first layer, consists of a nonbiodegradable, inert porous polymeric matrix in which a second active substance is dispersed.

The second layer, which is arranged in contact with the first layer, is either completely enveloped by the first layer, or only partially covered by it.

In the first case, the two layers are concentric.

In the second case, only one of the surfaces of the second layer is in contact with the first layer: in the text which follows, this type of tablet is designated as "containing parallel layers" and the shape of the tablet is unimportant and is in particular ovoidal. It should be understood that in this case, the two layers have one outer surface, their other surface being in contact with one another.

The tablets of the invention are preferably bilayered. However, the invention also encompasses multilayer tablets, as long as they comprise the combination of the first and second layers defined above.

For some active ingredients, problems of stability of the active ingredient included in the prolonged-release matrix may exist. In this case, it is advantageous to opt for the preparation of tablets containing concentric layers.

The kinetics of release of the active ingredient depend, in each case, on the exact composition of the layer considered. It is by adapting the nature and the quantity of the excipients constituting the two layers that the kinetics of release can be modulated.

One characteristic of the first layer is that it disintegrates rapidly at the site of administration. In contrast, the second layer is not biodegradable. Its matrix is inert in the sense that it does not react with the surrounding medium. The matrix of the second layer retains its physical and chemical integrity throughout the prolonged release of the active ingredient, regardless of the pH variations.

Since the first layer disintegrates instantly upon contact with an aqueous medium such as a physiological medium, it is easy to understand why the release of the first active substance is immediate.

In the case of the second layer and since the matrix constituting it is inert (it does not become eroded and does not swell in an aqueous medium), the release of the second active substance occurs by lixiviation and diffusion. The surrounding aqueous medium gradually penetrates into the inert porous matrix and then progressively, this aqueous medium dissolves the active substance dispersed in the inert matrix. The mechanism of diffusion being slow in essence, it can be understood why the release of the active ingredient is prolonged in this case.

Whereas the mechanism of disintegration of the first layer does not, or not to any great extent, depend on the nature of the active substance, it is clear that the more or less hydrophilic character of the active substance of the second layer can influence the kinetics of lixiviation/diffusion.

However, the invention is not limited as to the nature of the active substances. Each layer may contain a different active ingredient.

However, according to a specific embodiment of the invention, the first and second layers comprise the same active substance.

The active substances may be chosen in particular from any of the following groups (to designate the active substances, the international nonproprietary names have been adopted):

medicaments which are active in asthma such as 2-ethoxymethyl-4(3H)-pteridinone and bronchodilators such as theophylline, and/or some anti-inflammatory agents or antihistaminics of the ketotifen type;

medicaments which are active in the treatment of diabetes and its related complications of the neurological, nephrological, ocular or vascular type. By way of example, there may be mentioned metformin, hypolipidaemic agents such as fenofibrate or pravastatin and anti-atheromatous agents in general;

medicaments which are active in the treatment of alcoholism, such as acamprosate;

peripheral analgesics, for example para-aminophenol derivatives such as paracetamol, salicylated derivatives such as aspirin, diflunisal, propionic acid derivatives such as ibuprofen, fenoprofen, ketoprofen, aminoquinoline derivatives such as floctafenine, pyrazolone derivatives such as noramidopyrine;

central analgesics such as dextropoxyphene, codeine, morphine, pethidine, dextromoramide, buprenorphine, nalbuphine, pentazocine;

antispasmodics such as tiemonium, difemerine, phloroglucinol, trimebutine, pinaverium, prifinium;

nonsteroidal anti-inflammatory agents and, for example:
  arylpropionic derivatives such as ketoprofen, ibuprofen, naproxen, flurbiprofen, alminoprofen, tiaprofenic acid,
  arylacetic derivatives such as diclofenac, fentiazac,
  arylcarboxylic derivatives such as fenbufen and etodolac,
  anthranilic derivatives or fenamates such as niflumic acid and mefenamic acid,
  indole derivatives such as indometacin and oxametacin,
  oxicams such as piroxicam, tenoxicam,
  pyrazole-containing derivatives such as phenylbutazone,
  indene derivatives such as sulindac;

steroidal anti-inflammatory agents such as corticoids of the prednisone, prednisolone and methylprednisolone type;

antibiotics of the beta-lactam type, such as penicillins, of the cephalosporin type, such as cefuroxime axetil, of the beta-lactamase inhibitor type, such as clavulanic acid, of the aminoglycoside type, such as neomycin, of the macrolide type, such as spiramycin, erythromycin, of the tetracycline type, such as minocycline and doxycycline, of the sulfamide type, such as sulfadiazine, of the quinolone type, such as pefloxacin;

antituberculous agents such as isoniazid, rifampicin, ethambutol, pyrazinamide;

polyenic antifungal agents such as amphotericin B, nystatin, imidazole-containing antifungal agents such as miconazole, ketoconazole, fluconazole, flucytosine, griseofulvin;

antiviral agents of the type including zidovudine, aciclovir, adamantane such as rimantadine, amantadine, and moroxydine;

beta-blockers such as acebutolol, celiprolol, atenolol, betaxolol, metoprolol, bisoprolol, propanolol, nadolol, timolol, tertatolol, sotalol, pindolol, penbutolol, carteolol, oxyprenolol, labetalol;

nitrated derivatives such as isosorbide dinitrate, isosorbide mononitrate, pentaerythrityl tetranitrate, erythrityl tetranitrate;

antianginals of the sydnonimine type, such as molsidomine and linsidomine, cardiotonics such as orciprenaline, or alternatively of the digitalin type, such as digoxin, digitoxin, diuretics such as furosemide, bumetanide, clopamide, of the thiazide type such as hydrochlorothiazide, xipamide, of the tienilic acid type, indapamide, cicletanine, spironolactone, canrenone, amiloride, triamteren;

conversion enzyme inhibitors such as captopril, enalapril, lisinopril, perindopril, quinalapril, ramipril, benazepril;

calcium inhibitors such as nifedipine-, nicardipine, nitrendipine, diltiazem, verapamil, bepridil;

antihypertensives such as rilmenidine, clonidine, methyldopa, dihydralazine, prasozine, uradipil, minoxidil;

antiarrhythmics such as quinidine, disopyramide, cibenzoline, propafenone, flecainide, aprindine, nadoxolol, mexiletine, bretylium, amiodarone;

antiischaemics such as naftidrofuryl, trimetazidine, pentoxyfilline, nicergoline, buflomedil, dihydroergotoxine, dihydroergocristine, dihydroergocryptine, moxisylyte, raubasine, vincamine, papaverine, nicotinic acid;

venotonics such as vitamin P;

hypotension correctors such as heptaminol;

hormones such as thyroid hormones of the levothyroxine sodium type;

medicaments stimulating gastroduodenal motor function, such as cisapride, domperidone;

antiemetics such as metoclopramide, metopimazine, aliprazide, odansetron, scopolamine;

antiulcer agents such as ranitidine, famotidine, nizatidine, cimetidine, omeprazole, of the antiulcer prostaglandin type such as misoprostol, sucralfate, aluminium hydroxide;

antidiarrhoeals such as loperamide, diphenoxylate, medicaments promoting bacterial flora and those promoting yeast flora;

intestinal antiseptics such as nitrofuran;

contraceptives such as oestroprogestogens;

antianaemic agents such as iron;

antihistaminics such as phenothiazine;

vitamins such as thiamine, nicotinamide, pyridoxine, biotin, ascorbic acid, cyanocobalamine, retinol, colecalciferol;

antiepileptics such as valproic acid, phenytoin, carbamazepine, ethosuximide, progabide, vigabatrin;

antimigraine agents such as oxetorone, indoramine, ergotamine, ergot of rye derivatives such as dihydroergotamine, methysergide, tricyclic derivatives such as pizotifen;

anticoagulants such as antivitamin K agents;

antiparkinsonians such as levodopa, selegiline, lisuride, bromocriptine, biperiden, orphenadrine, procyclidine, tropatepin, scopolamine;

anxiolytics derived from benzodiazepines such as clotiazepam, tofisopam, oxazepam, alprazolam, lorazepam, bromazepam, prazepam, buspirone, alpidem, hydroxyzine, meprobamate, febarbamate;

antidepressants such as quinupramine, desipramine, imipramine, clomipramine, amitriptyline, viloxazine, amineptine, fluvoxamine, fluoxetine, tianeptine, oxaflozane, maprotiline, mianserin, trazodone, medifoxamine, toloxatone, IMAOs;

hypnotics such as zopiclone, zolpidem, and benzodiazepine derivatives such as flunitrazepam, nitrazepam, triazolam, phenothiazine derivatives such as niaprazine, doxylamine, barbiturate derivatives such as butobarbital, amobarbital, phenobarbital;

normothymics such as lithium, valpromide;

neuroleptics such as thioxanthen, pimozide, loxapine, carpipramine, phenothiazine derivatives such as chlorpromazine, thioridazine, fluphenazine, butyrophenone derivatives such as haloperidol, penfluridol, pipamperone, benperidol, benzamide derivatives such as sulpiride, amisulpiride, tiapride, sultopride;

antimetabolites such as methotrexate, mercaptopurine, fluorouracil, cytarabine, hydroxo-urea, asparaginase;

alkylating agents such as busulfan, pipobroman, procarbazine, nitrogen mustard derivatives such as chlorambucil, cyclophosphamide, estramustine, melphalan, lomustine, fotemustine;

anticancer steroids such as methoxyprogesterone, gestonorone, norethisterone, diethylstilbestrol, dienestrol;

and more generally peptides having a therapeutic activity.

A pharmaceutically acceptable salt of any one of the salifiable active ingredients listed above may also be selected as active ingredient.

The content of active ingredient in the first layer will be determined according to the pathology to be treated.

This content may be high, it being possible for the active substance to represent up to 99.0% of the total weight of the first layer, and for example from 1 to 99.0% by weight, preferably from 85 to 95% of the total weight of the first layer.

The second layer may contain up to 98.5% by weight of active ingredient, for example from 1 to 95% by weight, better still from 60 to 80%.

Numerous immediate-release compositions are known in the art and persons skilled in the art may thereby be freely inspired for the production of the first layer.

Persons skilled in the art will choose in particular the constituents of the first layer so as to ensure rapid disintegration thereof upon contact with water or with a physiological fluids.

It is in particular known to incorporate into this type of layer a disintegrating agent whose role is to cause the disintegration of the tablet in the presence of water or of physiological fluids.

These disintegrating agents are normally included in the said layer in an amount of from 0 to 15% by weight, preferably from 2 to 5% by weight. Examples of such disintegrating agents are: alginic acid, carboxymethylcellulose calcium, carboxymethylcellulose sodium, anhydrous colloidal silica, croscarmellose sodium, crospovidone, guar gum, magnesium and aluminium silicate, methyl cellulose, microcrystalline cellulose, potassium polacrilin, cellulose, pregelatinized starch, sodium alginate, starch sodium glycolate, starch and the effervescent mixtures known in the art for their disintegrating action.

The effervescent mixtures form part of the substances capable of rapidly causing the disintegration of the first layer, especially when the latter comes into contact with the gastric acids. These mixtures generally contain alkali metal or alkaline-earth metal carbonates or bicarbonates or sodium glycine carbonate.

Other additives may be incorporated into the immediate-release layer, such as diluents, binders, lubricants, antioxidants, colourings, sweeteners, flavourings and acidulants, wetting agents, hydrophilizing agents such as sorbitol and cyclodextrins, osmotic agents such as mannitol, pH correctors, stabilizing agents such as trehalose and mannitol, adsorbants, chelating and sequestering agents and gastroresistant film-coating excipients of the type including cellulose acetylphthalate and polymethacrylates.

By way of example, there may be chosen any one of the following diluents or alternatively a combination thereof: calcium carbonate, calcium sulfate, sucrose, dextrates, dextrin, dextrose, dicalcium phosphate dihydrate, kaolin, magnesium carbonate, magnesium oxide, maltodextrin, cellulose, microcrystalline cellulose, sorbitol, starches, pregelatinized starch, talc, tricalcium phosphate and lactose.

Among the binders, there may be mentioned: gum arabic, gum tragacanth, guar gum, alginic acid, sodium alginate, sodium carboxymethylcellulose, dextrin, gelatin, hydroxyethylcellulose, hydroxypropylcellulose, liquid glucose, magnesium and aluminium silicate, maltodextrin, povidone, pregelatinized starch, starch and zein.

The lubricants are glidants (such as anhydrous colloidal silica, magnesium trisilicate, magnesium silicate, cellulose, starch, talc or tricalcium phosphate) or alternatively anti-friction adhering agents (such as calcium stearate, glyceryl monostearate, glyceryl palmitostearate, hydrogenated vegetable oils, paraffin, magnesium stearate, polyethylene glycol, sodium benzoate, sodium lauryl sulfate, fumaric acid, stearic acid or zinc stearate and talc).

As examples of antioxidants, persons skilled in the art may select any of the following compounds: ascorbic acid, ascorbyl palmitate, fumaric acid, propyl gallate, sodium ascorbate and sodium metabisulfite, alpha-tocopherol, malic acid, BHA and BTH.

Preferred wetting agents are:

sodium docusate and sodium lauryl sulfate which are anionic surfactants;

benzalkonium chloride, benzethonium chloride and cetrimide which are cationic surfactants;

glyceryl monooleate, fatty acid esters of polyoxyethylene sorbitan, poly(vinyl alcohol) and sorbitans, which are nonionic surfactants.

Among the pH regulators, there are acidifying agents of the type including citric acid, hydrochloric acid, lactic acid, tartaric acid, as well as alkalinizing agents of the type including monoethanolamine, diethanolamine and triethanolamine, potassium citrate, sodium bicarbonate, sodium citrate dihydrate.

Examples of adsorbents are bentonite, anhydrous colloidal silica, kaolin, magnesium and aluminium silicate, microcrystalline cellulose and cellulose.

As chelating and sequestering agents, there may be used citric acid monohydrate, edetic acid, disodium phosphate, monosodium phosphate, potassium citrate, tartaric acid and sodium citrate dihydrate.

The quantities of these additives are those normally used in the art. Generally, the binder may represent from 0.5 to 25% by weight, better still from 2 to 5% by weight of the said first layer.

The lubricants are preferably incorporated into this first layer in an amount of 0.01 to 10% by weight.

As a guide, the quantity of gastroresistant film-coating excipients varies between 0.5 and 9% by weight.

It will be noted that all the abovementioned additives, with the exception of the disintegrating agents may also be added to the prolonged-release layer in similar proportions. The prolonged-release layer may, in addition, contain diluents chosen from glyceryl palmitostearate, hydrogenated vegetable oils, polymethacrylates, potassium chloride and sodium chloride.

Moreover, binders such as carbomer, ethyl cellulose, hydrogenated vegetable oils, hydroxypropylmethylcellulose, methyl cellulose and polymethacrylates may be incorporated into the prolonged-release layer.

However, the essential constituents of the second prolonged-release layer are polymeric materials which confer on it its inert and nonbiodegradable character. According to the invention, the polymeric materials in question are polymers or copolymers insoluble in water (but not forming a gel either upon immersion in an aqueous medium) which are discharged intact by the body.

These polymers may play the role of binder in the composition of the second layer.

Such materials are in particular polyvinyl chlorides, vinyl acetate/vinyl chloride copolymers, acrylonitrile/vinylidene chloride copolymers, polydimethylsiloxanes and copolymers derived from (meth)acrylic acids.

The copolymers derived from (meth)acrylic acids comprise the copolymers of derivatives of methacrylic acid and the copolymers of derivatives of acrylic acid and of derivatives of methacrylic acid. As derivatives of (meth)acrylic acids, esters are preferred.

According to a preferred embodiment of the invention, the nonbiodegradable inert polymeric material is chosen from the groups consisting of ethyl acrylate and methyl methacrylate copolymers, ethylammonium methacrylate and methyl acrylate copolymers, ethylammonium methacrylate and ethyl acrylate copolymers, ethylammonium methacrylate and methyl methacrylate copolymers, ethylammonium methacrylate and ethyl methacrylate copolymers, methacrylic acid and ethyl acrylate copolymers, methacrylic acid and methyl methacrylate copolymers.

According to the invention, "ethylammonium" is understood to mean a radical chosen from the ammonioethyl, ($C_1$–$C_4$) alkylammonioethyl, di ($C_1$–$C_4$) alkylammonioethyl and tri($C_1$–$C_4$)alkylammonioethyl groups. Preferably, ethylammonium designates a trimethylammonioethyl radical.

Such materials are commercially available, for example, from the company Röhm.

There may be mentioned, purely as a guide:

the copolymers Eudragit RL 30 D®, Eudragit RS 30 D®, Eudragit RL PO® and Eudragit RS PO®, Eudragit RL 12.5®, Eudragit RS 12.5®, Eudragit RL 100® and Eudragit RS 100®, which are copolymers of esters of acrylic acid and of esters of methacrylic acid, with a low content of ammonium groups. These polymers have as recurring unit:

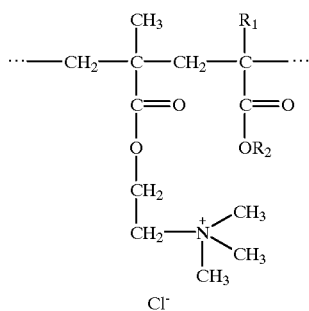

in which $R_1$ is a hydrogen atom or a methyl group and $R_2$ is the methyl or ethyl group;

the copolymer Eudragit NE 30 D® which is a neutral copolymer of ethyl acrylate and methyl methacrylate, in which the recurring unit has the formula:

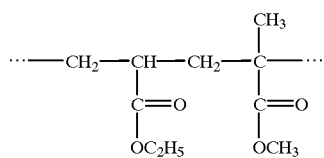

the copolymers Eudragit L 30 D-55® and Eudragit L100-55® which are copolymers of methacrylic acid and ethyl acrylate, in which the recurring unit has the formula:

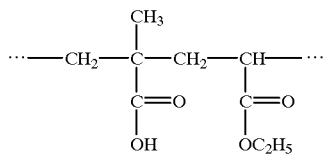

the copolymers Eudragit L 100®, Eudragit L 12.5®, Eudragit S 100® and Eudragit S 12.5® which are copolymers of methacrylic acid and methyl methacrylate in which the recurring unit has the formula:

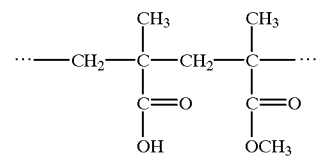

Among these polymers, the copolymer NE 30 D® has proved particularly advantageous. In general, the copolymers of esters of methacrylic acid and of esters of acrylic acid are used in preference to any other type of inert matrix.

The molecular mass of the polymeric material used may vary to a large extent depending on the nature of the monomers constituting the material.

In the case of the copolymers derived from acrylic and/or methacrylic acid mentioned above, the average molecular mass is between 100,000 and 1,000,000, preferably between 130,000 and 800,000.

It is desirable that the quantity of inert polymeric materials does not exceed 25% of the total weight of the second layer, and is not less than 1% of the total weight of this layer. Preferably, the quantity of polymeric materials varies between 2.5% and 12% of the total weight of the second layer.

The whole tablet may be coated with a gastroresistant or enterosoluble polymeric film, such that the active ingredient is released only in the duodenal tract.

The polymeric substances generally used for the production of the gastroresistant systems are cellulose acetophthalate, cellulose acetopropionate, cellulose trimellitate or polymers and copolymers of (meth)acrylic acids.

The tablets of the invention are conventionally prepared by a method including the steps of granulation, followed by compression.

More precisely, the method of preparation, which is the subject of the invention, comprises the steps consisting in:

a) preparing a granule of a first active substance from a pulverulent mixture of the said first active substance, a disintegrating agent and one or more additives suitable for the preparation of a layer for the immediate release of the said active substance;

b) preparing a granule of a second active substance from a pulverulent mixture of the said second active substance, from one or more nonbiodegradable inert polymeric materials and from one or more additives suitable for the preparation of a layer for the prolonged release of the said active substance;

c) combining, by compressing, in a manner known per se, the two types of granule obtained in steps a) and b) above so as to obtain tablets in which the first layer, affording immediate release, results from the compression of the granule obtained in step a), and, having a second layer arranged in contact with the said first layer, the said second layer resulting from the compression of the prolonged-release granule obtained in step b).

The first step (step a)) is designed to provide a granule based on the first active substance, which will lead, through compression, to the first layer, called immediate-release layer.

The second step (step b)) is designed to provide a granule based on the same active substance or on a different active substance, which will lead, through compression, to the second layer, called prolonged-release layer. The constituents of this layer are those of the nonbiodegradable inert polymeric matrix defined above.

Step c) leads to the formation of the tablet through successive compression of the granules obtained in the preceding steps a) and b).

Steps a) and b) involve the granulation of powders of amorphous or crystallized particles. This granulation is carried out in a manner known per se and, for example, by a wet granulation method.

The method of granulation comprises five essential steps: (i) dry-mixing of its various constituents, (ii) wetting, (iii) granulation proper, (iv) drying, and then (v) sizing.

The dry-mixing consists in mixing the pulverulent excipients entering into the composition of the granule.

The wetting consists in adding to the pulverulent mixture various constituents, a wetting liquid which may be water, a ($C_1$–$C_4$)alkanol, an aqueous solution of binder or an alcoholic solution of binder. According to the invention, the expression "alcoholic solution of binder" includes both the alcoholic and aqueous-alcoholic solutions in which the solvent is a mixture of one or more ($C_1$–$C_4$)alkanols or a mixture of water and of one or more ($C_1$–$C_4$)alkanols. A preferred ($C_1$–$C_4$)alkanol is isopropanol. It is carried out in a kneading, planetary, mixing pan, projection or whirling-type mixer-blender or a rapid-type mixer-granulator.

In step a), the appropriate wetting liquid is water, a ($C_1$–$C_4$)alkanol, an aqueous solution of binder or an alcoholic solution of binder as defined above, and as generally recommended in the art.

In step b), it is possible to use an aqueous dispersion or an organic solution of the nonbiodegradable polymeric material(s) as wetting liquid. Better homogeneity of distribution of the matrix is thus obtained. "Organic solution" is understood according to the invention to mean a solution of the non-biodegradable polymeric material(s) in an organic solvent which is either a mixture of one or more ($C_1$–$C_4$)alkanols, or a mixture of one or more (($C_1$–$C_4$)alkyl) (($C_1$–$C_4$)alkyl) ketones and of one or more ($C_1$–$C_4$)alkanols. According to the invention, isopropanol is the preferred ($C_1$–$C_4$)alkanol. Likewise, when a mixture of ketone(s) and of alkanol(s) is used, the mixture of isopropanol and acetone is preferred.

When the polymeric material is a copolymer derived from acrylic and/or methacrylic acid, the dispersion or the solution will preferably have a viscosity of between 10 and 300 mPa.s, better still between 15 and 200 mPa.s.

According to a preferred embodiment of the invention, the sizing is carried out by passing over a screen with a mesh opening of between 0.5 and 1.5 mm, preferably of between 0.8 and 1.5 mm.

The preferred value of the mesh opening is 1.25 mm in each of steps a) and b).

However, the invention is not limited to carrying out a wet granulation method. Thus, persons skilled in the art will also be able to use the other existing granulation methods, such as the dry granulation method.

The last step (step c)) leads to the formation of the tablet. The combination of the granules is carried out in a conventional manner using the granules obtained in steps a) and b).

In the case of bilayer tablets, containing concentric layers, this step involves (i) compression, in a first compression chamber, of the entire prolonged-release granule obtained in step b) for the production of a core tablet; (ii) the compression, in a second compression chamber, of a portion, preferably 50% by weight, of the immediate-release granule obtained in step a) above; (iii) the introduction and the positioning of the core tablet resulting from step (i) above in the said second compression chamber; (iv) the application of a gentle compression with centring of the core in the said second compression chamber; (v) the addition of the remainder of the immediate-release granule to the said second granulation chamber; and (vi) the conjoint compression of the immediate-release granule on the tablet formed in step iv) above.

In the case of bilayer tablets, containing parallel layers, step c) comprises: (i) a gentle compression of the entire prolonged-release granule in a compression chamber; and then (ii) the addition of the entire immediate-release granule to the said compression chamber and its positioning on the tablet resulting from step i) above; and (iii) the final compression of the tablet.

The respective proportions of the immediate-release and prolonged-release granules are not critical according to the invention.

The tablets of the invention may be administered by the oral or vaginal route. They allow the immediate release of a first active substance, and then the release of a second active substance, which is optionally identical to the first, over a period of 2 to 12 h.

The multilayer tablets of the invention are particularly advantageous since their method of preparation is simple, the excipients constituting them being customary. Furthermore, it is possible, by appropriately selecting the nonbiodegradable inert polymeric materials, to vary the dissolution profiles to a very large extent and with precision, depending on the needs.

According to the preferred embodiment of the invention, the polymeric materials belong to the Eudragit series marketed by the company Röhm, which are copolymers derived from methacrylic and/or acrylic acid. Because of the diversity of the properties of these copolymers, it is possible to obtain modulation of the release profile of the active ingredients.

In addition, these copolymers confer on the resulting tablets excellent formulation capacity (possibility of incorporating high levels of active ingredients) and compression capacity.

The choice of such copolymers offers, in addition, the possibility of film-coating the tablets with excipients of the Eudragit type in order to obtain a gastroresistant coating.

On the other hand, these copolymers are absolutely inert in relation to the body, which ensures release of the active ingredient independently of the influence of the body (and in particular of pH variations) and therefore reliability, safety, quality, reproducibility and better tolerance of the effects linked to the administration of the tablets of the invention.

The examples provided in the text which follows illustrate the invention more clearly. Reference will be made to the accompanying FIGS. 1 and 2.

EXAMPLE 1 a) Preparation and formulation of the immediate-release granule

The active ingredient is 2-ethoxymethyl-4(3H)-pteridinone, designated as EMP in the text which follows.

The constituents for the preparation of the immediate-release granule, designated as GLI-1 in the text which follows, were used in the following proportions by weight:

| EMP | 94.12% |
|---|---|
| Polyvinylpyrrolidone 30 | 2.94% |
| Cross-linked carboxymethylcellulose | 2.94% |
| Total | 100.00% |

The active ingredient, polyvinylpyrrolidone 30, and the carboxymethylcellulose are introduced into a mixer-granulator for a 3-minute mixing.

The wetting liquid, osmosed water, is then introduced into the mixer-granulator until well-formed grains and agglomerates are obtained. Next, the whole is dried (oven or fluidized air bed) and sized on a screen with a mesh opening of 1.25 mm.

b) Preparation and formulation of the prolonged-release granule

The active ingredient is that used in Example 1.

The nonbiodegradable polymeric material used is Eudragit NE 30 D® marketed by the company Röhm.

The constituents for the preparation of the prolonged-release granule, designated as GLP-1 in the text which follows, were used in the following proportions by weight:

| EMP | 71.70% |
|---|---|
| Fine lactose powder | 17.20% |
| Eudragit NE 30 D ® | 8.80% |
| Talc | 1.10% |
| Magnesium Stearate | 1.20% |
| Total | 100.00% |

The active ingredient and the lactose are introduced into a mixer-granulator for a 3-minute mixing.

The Eudragit NE 30 D®, which is an aqueous dispersion of a neutral copolymer of ethyl acrylate and methyl methacrylate, is then gradually introduced into the mixture, as wetting liquid. Purified water is added, if necessary, in order to obtain well-formed granules comprising agglomerates. Next, the granule is dried in a fluidized air bed and sized on a screen with a mesh opening of 1.25 mm. The lubricants (talc and magnesium stearate) are then mixed with the granule obtained above for 40 seconds.

c) Preparation of tablets containing concentric layers and of so-called tablets containing parallel layers The following tablets containing parallel layers A to D are obtained using the following steps by means of a compressing machine provided with ovoid dies:

(i) by gentle compression, in a compression chamber, of the entire prolonged-release granule of Example 1b); and (ii) by addition, in the same compression chamber, of the entire immediate-release granule of Example 1a) over the tablet obtained in step (i); and (iii) by subsequent compression of the whole consisting of the immediate-release granule of Example 1a) and of the tablet obtained in step (i) above.

The following tablet containing concentric layers E was obtained using the following steps:

(a) the compression, in a first compression chamber, of the entire prolonged-release granule of Example 1b) for the production of a core tablet;

(b) the compression of a fraction of the immediate-release granule of Example 1a) in a second compression chamber (about half);

(c) the transfer of the tablet resulting from step (a) into the second compression chamber;

(d) the application of a gentle compression with centring of the tablet of step (a) in the said second compression chamber;

(e) the addition of the remainder of the immediate-release granule of Example 1a) to the second compression chamber, and (f) the conjoint compression of the immediate-release granule of Example 1a) and of the tablet resulting from step (d) above.

Table 1 below indicates, for each tablet, the respective quantities of granules used.

TABLE 1

| Tablet (reference) | Quantity of GLI granules (mg) | Quantity of GLP granules (mg) | Unit weight of the tablet (mg) |
|---|---|---|---|
| A | 425.0 | 558.0 | 983.0 |
| B | 531.2 | 697.5 | 1228.7 |
| C | 318.7 | 976.3 | 1295.0 |
| D | 318.7 | 697.5 | 1016.2 |
| E | 531.2 | 558.0 | 1089.2 |

EXAMPLE 2

Dissolution Profiles for the Tablets Manufactured According to the Procedure of Example 1

The dissolution profiles for the tablets manufactured in the preceding example were determined by UV spectrometry.

The tablet to be tested is introduced into a reactor previously charged with one litre of osmosed water, at 37° C., and provided with a temperature-regulating system and with an effective stirring system.

During the whole experiment, the reactor is kept stirring at 37° C.

At regular intervals of time t, samples of the medium contained in the reactor are collected, filtered on a filter with a porosity of 0.45 µm, and analysed by UV spectrometry.

Conditions for Analysis by UV Spectrometry

The optical density of the samples collected, diluted in a known volume of osmosed water, is measured at 313 nm.

The quantity of active ingredient q present in the sample is determined by comparison with the optical density of a control solution of the active ingredient, EMP, of known concentration. A simple calculation makes it possible to find the total quantity of active ingredient released in the reactor at the instant t.

The dissolution profile for a tablet tested is obtained by plotting, on a curve, the calculated quantities of active ingredient as a function of the time of collection.

Figure 2:
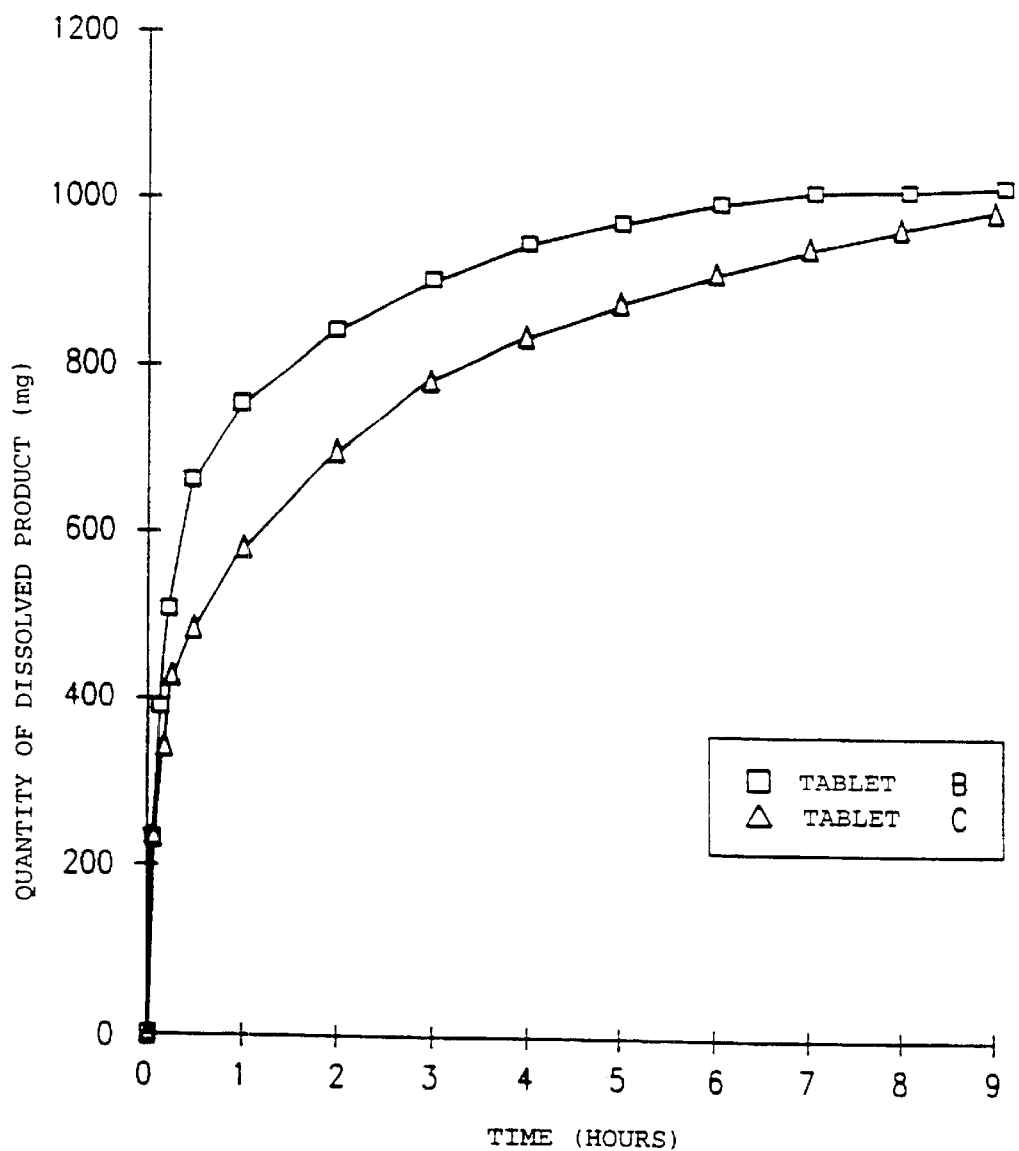
Figure 3:
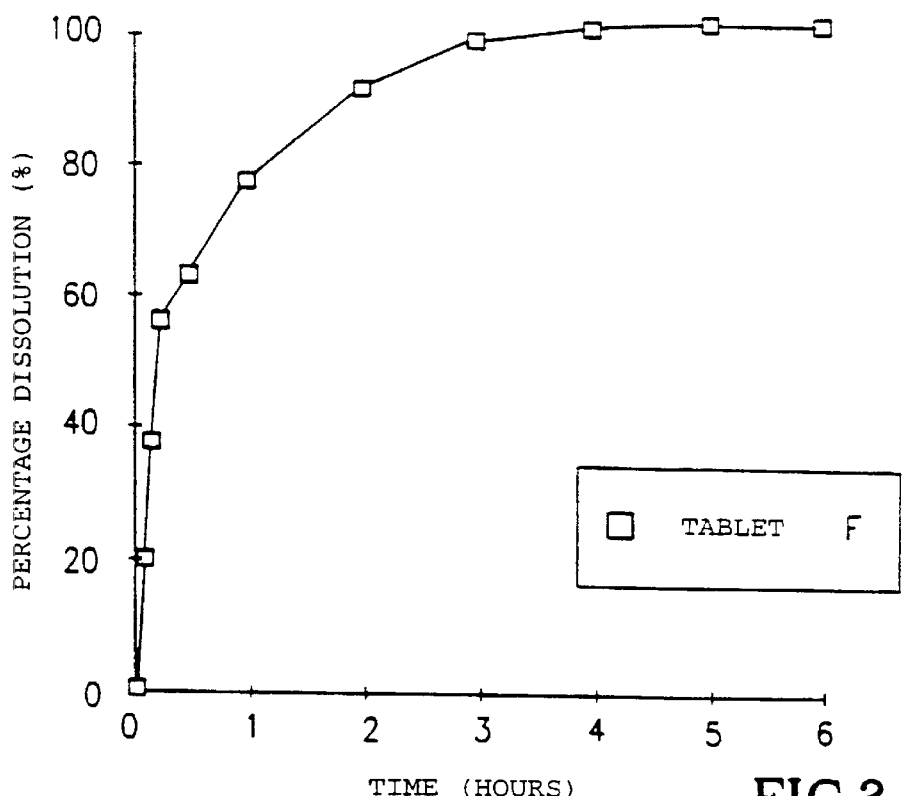
Figure 4:
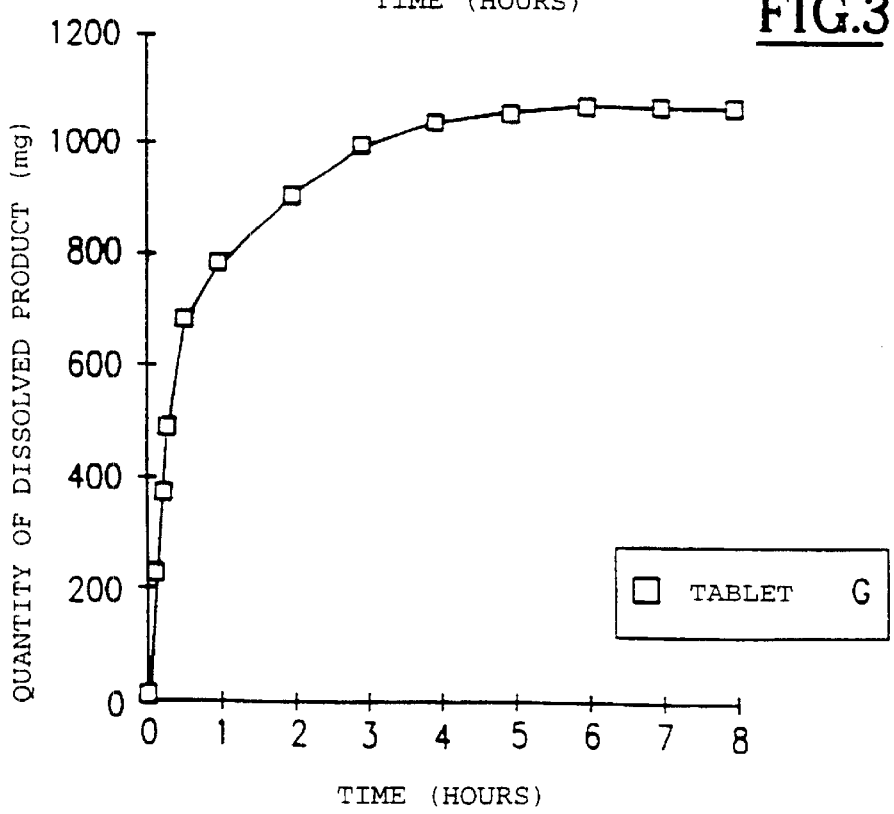
Figure 5:
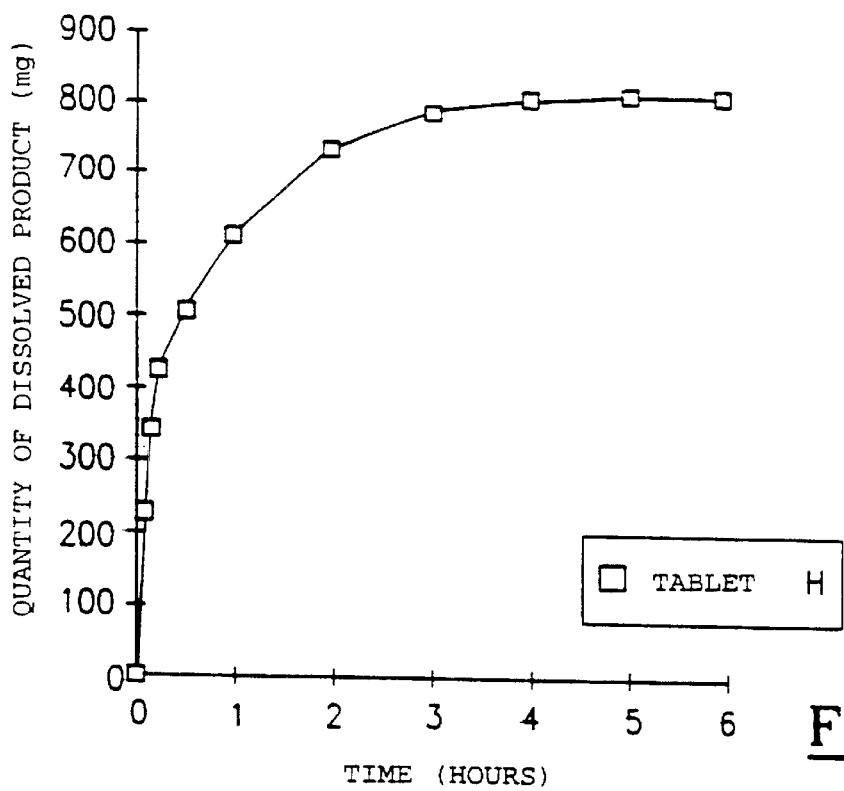
Figure 6:
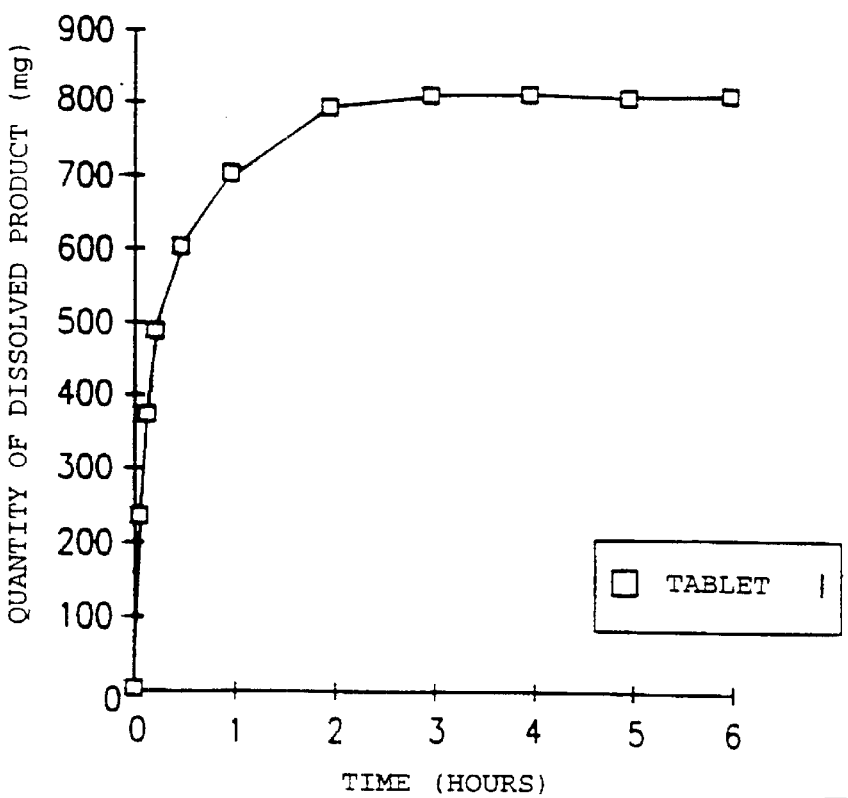

The accompanying FIGS. 1 and 2 show the dissolution profiles plotted in the cases of tablets A to E above.

EXAMPLE 3

By following the operating protocol described in Example 1, the tablets containing parallel layers F to I in the following Table 2 are prepared:

TABLE 2

| Tablet | Type of immediate-release granules | Quantity of immediate-release granules (mg) | Type of prolonged-release granules | Quantity of prolonged-release granules (mg) |
|---|---|---|---|---|
| F | GLI-2 | 327.9 | GLP-2 | 836.8 |
| G | GLI-2 | 546.4 | GLP-3 | 697.35 |
| H | GLI-2 | 327.9 | GLP-4 | 697.35 |
| I | GLI-2 | 437.15 | GLP-4 | 557.9 |

The formulation of the immediate-release granules, GLI-2, is given below:

| | |
|---|---|
| EMP | 91.5% |
| Polyvinylpyrrolidone 30 | 4.0% |
| Cross-linked carboxymethylcellulose | 4.0% |
| Magnesium stearate | 0.5% |
| TOTAL | 100% |

These granules are prepared using the operating protocol of Example 1a).

The formulations of the prolonged-release granules are given below:

GLP-2

| | |
|---|---|
| EMP | 71.7% |
| Fine lactose powder | 16% |
| Eudragit RSPO | 10% |
| Talc | 1.1% |
| Magnesium stearate | 1.2% |
| TOTAL | 100% |

GLP-3

| | |
|---|---|
| EMP | 71.7% |
| Fine lactose powder | 17.2% |
| Eudragit RS30D | 8.8% |
| Talc | 1.1% |
| Magnesium Stearate | 1.2% |
| TOTAL | 100% |

GLP-4

| | |
|---|---|
| EMP | 71.7% |
| Fine lactose powder | 17.2% |
| Eudragit RSPO | 8.8% |
| Talc | 1.1% |
| Magnesium stearate | 1.2% |
| TOTAL | 100% |

These granules are prepared using the operating protocol of Example 1b).

EXAMPLE 4

The dissolution curves for tablets F to I were plotted using the operating protocol described in Example 2.

These curves are presented in FIGS. 3 to 6.

What is claimed is:

1. A multilayer tablet comprises at least two superposed layers, wherein:
   a first outer layer comprises a mixture of excipients and a first active substance, wherein the first layer allows immediate release of the first active substance;
   a second layer, which is in contact with the first layer, comprises at least one nonbiodegradable, inert porous polymeric matrix in which a second active substance is dispersed; wherein the second active substance is identical to the first active substance.

2. A tablet according to claim 1, wherein the nonbiodegradable inert polymeric matrix comprises one or more nonbiodegradable inert polymeric materials selected from polyvinyl chlorides, vinyl acetate/vinyl chloride copolymers, copolymers derived from acrylic and/or methacrylic acids, acrylonitrile/vinylidene chloride copolymers and poydimethylsiloxanes.

3. A tablet according to claim 2, wherein the copolymers derived from methacrylic and/or acrylic acids are selected from copolymers of esters of ethyl acrylate and methyl methacrylate, ethylammonium methacrylate and ethyl acrylate copolymers, ethylammonium methacrylate and methyl methacrylate copolymers, ethylammonium methacrylate and ethyl methacrylate copolymers, methacrylic acid and ethyl acrylate copolymers, methacrylic acid and methyl methacrylate copolymers.

4. A tablet according to claim 2, wherein the second layer comprises 1 to 25% by weight of said nonbiodegradable inert polymeric materials.

5. A tablet according to claim 1, wherein the second layer comprises 1 to 98.5% by weight of the second active substance.

6. A tablet according to claim 1, wherein the first layer further comprises one or more disintegrating agents.

7. A tablet according to claim 1, wherein the first layer comprises 1 to 99.0% by weight of the first active substance.

8. A tablet according to claim 1, wherein the second layer has a top surface and a bottom surface, only one of those surfaces being in contact with the first layer.

9. A tablet according to claim 1, wherein the first layer and the second layer are concentric.

10. A method for preparing a tablet according to claim 1, comprising:
    a) preparing a granule of a first active substance from a pulverulent mixture of the said first active substance, a disintegrating agent and optionally one or more additives suitable for the preparation of a layer for the immediate release of the first active substance;
    b) preparing a granule of a second active substance from a pulverulent mixture of the said second active substance, one or more nonbiodegradable inert polymeric materials and optionally one or more additives suitable for the preparation of a layer for the prolonged release of the said second active substance; and c) combining, by compressing, the granules obtained in steps a) and b) to obtain tablets in which the first layer, results from the compression of the granule obtained in step a), and the second layer results from the compression of the granule obtained in step b).

11. A tablet according to claim 1, wherein the active substance is 2-ethoxymethyl-4(3H)-pteridinone.

12. A tablet according to claim 6, wherein said disintegrating agents are selected from alginic acid, carboxymethylcellulose calcium, carboxymethylcellulose sodium, anhydrous colloidal silica, croscarmellose sodium, crospovidone, guar gum, magnesium and aluminium silicate, methyl cellulose, microcrystalline cellulose, potassium polacrilin, cellulose, pregelatinized starch, sodium alginate, starch sodium glycolate, starch and effervescent mixtures having disintegrating action.

13. A tablet according to claim 1, further comprising a coating of gastro resistant or enterosoluble polymeric film.

14. A tablet according to claim 1, wherein the second layer is completely enveloped or partially covered by the first layer.

15. A tablet according to claim 1, comprising one or more of diluents, binders, lubricants, antioxidants, colorings, sweeteners, flavorings, acidulants, wetting agents, hydrophilizing agents, osmotic agents, pH correctors, stabilizing agents, gastroresistant film-coating excipients, absorbents, chelating and/or sequestering agents.

16. A method for treating asthma comprising administering a tablet of claim 1 to a patient.

17. A method for treating asthma comprising administering a tablet of claim 11 to a patient.

18. A tablet according to claim 1, wherein the second layer comprises 1 to 95% by weight of the second active substance.

* * * * *